United States Patent [19]

DiNello et al.

[11] Patent Number: 4,687,735
[45] Date of Patent: Aug. 18, 1987

[54] ENZYMATIC POLY-REACTANT CHANNELING BINDING ASSAY

[75] Inventors: Robert K. DiNello, Cupertino; Ian Gibbons, Palo Alto; Edwin F. Ullman, Atherton, all of Calif.

[73] Assignee: Syntex (U.S.A.) Inc., Palo Alto, Calif.

[21] Appl. No.: 474,906

[22] Filed: Mar. 14, 1983

[51] Int. Cl.[4] ........................................... G01N 33/535
[52] U.S. Cl. ........................................... 435/7; 435/4; 435/25; 435/28; 435/188; 435/810
[58] Field of Search .................. 435/4, 7, 25, 28, 188, 435/810

[56] References Cited

U.S. PATENT DOCUMENTS 4,233,402 11/1980 Maggio et al. ........................... 435/7

Primary Examiner—Sidney Marantz
Attorney, Agent, or Firm—Bertram I. Rowland; Theodore J. Leitereg

[57] ABSTRACT

Improved sensitive immunoassays are provided involving channeling involving one, usually two enzymes, where the enzymes are related by the product of one enzyme being the substrate of the other enzyme. A dispersed aggregation is formed in the assay medium of (1) the analyte, (2) one of the enzymes bound to a second binding member ("SBM") (enzyme - SBM conjugate) which conjugate is non-covalently bound to a first binding member ("FBM"), and (3) a multiplied amount of the other enzyme bound in the complex. The large amount of enzyme or reactant in the complex is achieved by having a multiplicity of linkages binding the enzyme or reactant directly or indirectly to FBMs. The enzyme channeling provides for a detectable signal which can be related to the amount of analyte in the medium.

17 Claims, No Drawings

ENZYMATIC POLY-REACTANT CHANNELING BINDING ASSAY

BACKGROUND OF THE INVENTION

1. Field of the Invention

An important component in the diagnosis and treatment of disease is the ability to determine the nature of the pathogen, the strain of the pathogen, the affected cells, the presence of abnormal proteins, and the like, as well as the ability to determine the level of bound or unbound drug in a physiological fluid, during the treatment of a disease. Determination of drugs is also of interest in cases of drugs of abuse, the ingestion of toxins, and the like. Also, in many instances, one is concerned with the presence of specific receptors, particularly antibodies, in relation to disease diagnosis or determining the health of the individual. Assays also find use in blood typing, HLA typing and the determination of other phenotypic products.

In many situations, one is concerned with detecting an extremely small amount of material in a complex composition containing a variety of other materials, which may be of similar or different structure. In order to detect the presence of a specific material, antibodies or other receptors have been employed which bind specifically to a determinant site. This complex formation between a ligand and receptor has found extensive use for a qualitative or quantitative determination of the presence of a defined determinant site in a sample.

More recently, there is increasing interest in the ability to detect pathogens, mutations and genetic related diseases by polynucleotide hybridization. Since there will frequently be concern in detecting unique sequences which are only a minute part of the total DNA and/or RNA, sensitive methods will be necessary to ensure accuracy of results.

As the need has grown to detect an ever increasing variety of analytes, there has been increased efforts to develop new techniques with enhanced sensitivity, ease of operation, opportunity for automation, reproducibility and low incidence of error.

DESCRIPTION OF THE PRIOR ART

U.S. Pat. No. 4,233,402 describes a homogeneous channeling assay. U.S. Pat. No. 4,299,916 describes a heterogeneous channeling assay. Stuart and Porter, Exp. Cell. Res. (1978) 113:219–222, describe monoclonal antibodies to DNA-RNA hybrid complexes. Other references include copending application Ser. No. 373,760, filed Apr. 30, 1982, now abandoned, which concerns an agglutination dependent enzyme channeling immunoassay involving particles.

SUMMARY OF THE INVENTION

Novel assays are provided which involve enzymatic production of a product which interacts with a second component of a signal producing system. The enzyme is conjugated to a member of a specific binding pair. The second component is polymerized under conditions where the enzyme is included in the polymer only as the conjugate bound to its reciprocal binding member. The high mole ratio second component to enzyme in the polymer provides for an enhanced signal for each binding event. The observed signal is related to the amount of analyte in a sample by comparison with standards.

DESCRIPTION OF THE SPECIFIC EMBODIMENTS

In accordance with the subject invention, a novel, sensitive assay technique employing channeling is provided for the determination of analytes, particularly at low analyte concentrations. The method involves at least one enzyme, normally two enzymes, where the two enzymes are related by the product of one being the substrate of the other.

The subject invention is predicated on the employment of a signal producing system involving at least three members. The three members include an enzyme, its substrate, and a material which interacts with a product of the enzyme. The signal producing system component which interacts with the product of the enzyme can itself be a different enzyme which interacts with the product of the first enzyme in a manner which provides a change in a measurable signal or may be a reactant, which reacts with the product of the first enzyme, to result in a change in a measurable signal.

The subject invention provides a number of advantages in that the molecules involved in the signal producing system are, for the most part, relatively small molecules, as compared to most particles. Thus, the molecules enjoy a rapid rate of diffusion in the assay medium. Employing an enzyme, provides for a large amplification, which in the present invention will be associated with a binding event. By polymerizing a member of the signal producing system, a large amount of such member will be brought into close proximity. By further providing that the first enzyme will be incorporated in the polymer by virtue of a binding event between specific binding members, one brings the first enzyme into close proximity to a high multiple and localized concentration of the subsequent component of the signal producing system, which interacts with the product of the first enzyme, or, if it is an enzyme, may produce a product which is acted upon by the first enzyme. In effect, one can enjoy the high concentration of a label or reactant which is achieved by employing particles, while avoiding the problem of the slow diffusion of the particles. In this manner, the sensitivity of the assay is greatly enhanced and a large signal can result from a single binding event.

One may divide the signal producing system into two major categories: enzyme channeling; and enzyme product reaction. The preferred method would be the enzyme channeling system.

The binding event involves members of a specific binding pair which will be ligands and receptors, which will be arbitrarily referred to without indicating which members intended as a first binding member ("FBM") and a second binding member ("SBM"). The first enzyme will be conjugated to a SBM to provide an enzyme-SBM conjugate. The enzyme of the enzyme-SBM conjugate will be in limited amount based on the limited number of available binding sites of the FBM.

The other enzyme will be part of a system that involves polymerization of the other enzyme used, that includes the enzyme-SBM conjugate in the polymer to an extent related to the extent of complex action between the enzyme-SBM conjugate and FBM. In effect, a substantial proportion of the total other enzyme in the assay medium becomes involved in colloidal copolymeric aggregates.

By the appropriate choice of enzymes, one can provide for a high localized concentration of substrate of the second enzyme in the catalytic sequence or one can ensure that a substantial fraction of the product produced by the first enzyme in the catalytic sequence is consumed by the second enzyme in the aggregate. In this way, great sensitivity is produced by having the observed signal related to the amount of analyte present in the assay medium greatly enhanced as compared to the background signal resulting from production of product unrelated to the amount of analyte in the medium. Optionally, one may use a scavenger in the bulk solution to further reduce background signal. Furthermore, since the binding of SBM to FBM occurs in a homogeneous solution prior to formation of particles, binding occurs more rapidly than when the binding rate is limited by diffusion to a surface, such as a wall or particle.

The assay can measure both first and second binding members. Where SBM is the analyte, one can have a predetermined amount of FBM included in the reagents employed, where the amount of SBM reduces the amount of enzyme-SBM in the copolymeric aggregate. Usually FBM will be the analyte, so that the amount of enzyme-SBM in the copolymeric aggregate will be directly related to the amount of analyte in the assay medium. Thus, where FBM is the analyte, the observed change in signal will usually increase with increasing amounts of FBM.

A wide variety of interactions can be provided for by varying the nature of the enzymes and their substrates. One can provide for activation by the production of a co-effector, deactivation by production of an inhibitor, or deactivation, where the two enzymes compete for the same substrate, but only the enzyme of the enzyme-SBM conjugate results in a product producing a detectable signal.

The enzyme channeling reaction is predicated upon two enzymes communicating, so that the product of a first enzyme is the substrate of a second enzyme. The second enzyme produces a product which results in a change in a detectable signal as compared to a standard. By virtue of having the two enzymes of the channeling system in close proximity, an enhanced rate will be observed for formation of the product that provides for the change in the observed signal. Furthermore, by having a high concentration of one of the enzymes in proximity to the other enzyme, the production of the signal producing product in the aggregation will be much greater than the production of such product in the bulk solution.

In many instances, enzymes will have substantially different turnover rates, so that it is desirable to have a plurality of one enzyme in relation to the other enzyme. In other situations, one wishes to maximize the rate of turnover of an enzyme by having a high localized concentration of the substrate. Another consideration is whether one can have one enzyme substantially surrounded by the other enzyme, so that one minimizes the amount of the intermediate substrate which diffuses into the solution. Furthermore, by substantially sweeping the assay medium, so that a substantial proportion, preferably a major proportion, of one of the enzymes is involved in the aggregations, the background can be substantially reduced. Also, one may further reduce the background by employing a scavenger in the bulk medium.

One of the enzymes will be bound to a SBM, normally covalently bound, so that for each binding site to which the SBM binds, one or a few enzymes will become non-covalently bound to the FBM. The other enzyme will be part of a system which provides for the copolymerization of the other enzyme with the complex of the FBM and enzyme-SBM conjugate. In effect, one provides a linking system which provides for block polymerization or copolymerization of one of the enzymes with intermittent incorporation of the complex in the polymeric aggregation. The FBM, will be polyvalent, that is have a plurality of binding sites, or be provided in a polyvalent form, that is, having a plurality of FBM's joined together.

Various configurations and reagents may be employed to provide the desired polymeric aggregation. Once aggregates have begun to form or have been formed, by adding the appropriate substrate and other reagents, the formation or destruction of a product providing a detectable signal can be achieved. The signal may then be determined in relation to standards, and the presence or amount of particular analyte may be determined.

Definitions

Analyte—The compound or composition to be measured, which may be a first binding member or second binding member, where the first and second binding members are a specific binding pair. One of the binding members will be a ligand or polynucleotide. The other binding member will be a receptor or polynucleotide which is homologous or complementary to the first binding member.

First Binding Members and Second Binding Members ("FBM" and "SBM", respectively)—The first and second binding members are organic compounds which are members of a specific binding pair and are reciprocal to each other. The compounds are ligands and receptors, where ligands are any organic compound for which a receptor is plurality of sites to which the receptor binds. The sites may be referred to as determinant sites or epitopic sites, which define a particular spatial and polar organization to which the reciprocal or homologous receptor binds. Depending upon the nature of the receptor, the receptor may be a macromolecular polypeptide or a polynucleotide, either DNA or RNA, usually having at least about ten bases. The receptor will bind to a specific polar and spatial organization of the ligand, having a surface complementary to a number of features of the ligand surface. The polynucleotide receptor will have a sequence of bases where all, or substantially all, of the bases are complementary to the ligand polynucleotide.

For the purposes of the subject invention, the focus of the FBMs and SBMs is their ability to specifically bind to one another. Therefore, a variety of receptors are treated as equivalent in having the same binding specificity. For example, antibodies, enzymes, natural receptors, or the like may be useful for binding to the same ligand. In addition, fragments of a receptor, such as a Fab, F(AB')$_2$ or F$_v$ will be equivalent to the intact antibody for the purpose of this invention. In addition, the various types of immunoglobulins may be interchangeable in various situations.

Similarly, with large ligands, it may be feasible to use only the portion of the ligand associated with the determinant site or epitope, rather than the entire ligand in some instances.

Modified Second Binding Member ("modified SBM")—The modified SMB will have covalently bonded to the SBM a label which is part of a linking system which involves the inclusion of the modified SBM in the polymeric aggregate. The modification may be as a result of covalent or non-covalent binding to the SBM to provide for the multiplicity of the member of the signal producing system in the copolymer aggregate.

Signal Producing System—The signal producing system involves at least three members, the essential members being an enzyme, a substrate for the enzyme which produces a product, and an interacting member which interacts with the enzyme product to provide for a change in a measurable signal in the assay medium. The interacting member may be a second enzyme which employs the product of the first enzyme as a substrate or may be a chemical compound which reacts with the product of the enzyme to produce a product which provides for a change in a detectable signal. Of the three essential members of the signal producing system, two will be involved in the polymeric aggregate with one of the two at a high molar multiple to the other. For the most part, the two members in the polymeric aggregate will be enzymes, involved in an enzyme channeling reaction, although one of the enzymes may be substituted with a compound which can react with the product of the other enzyme.

Linking System—The linking system provides a method for polymerizing a member of the signal producing system, which is either an enzyme or a compound which reacts with a product of an enzyme to produce a change in a detectable signal. The polymeric aggregate will involve the polymerized member of the signal producing system and the enzyme bound to the SBM through the intermediacy of the FBM, providing for a high multiple of the polymerized signal producing system member to the enzyme bound to the SBM. In order for enzyme-SBM to be involved in the polymeric aggregate, it will be necessary that the FBM be polyvalent or provided in polyvalent form. For a hapten acting as the FBM, the hapten could be provided as a plurality of haptens joined together or the hapten joined to another molecule as a conjugate which molecule serves as the linking member to the copolymeric aggregate.

Ligand Analog—A modified ligand which can compete with the analogous ligand for a receptor, the modification providing means to join a plurality of ligand analogs in a single entity or to provide a means for binding to a label. The ligand analog will differ from the ligand by more than replacement of a hydrogen with a bond which links the ligand analog to a hub nucleus or label.

Poly(ligand analog)—A plurality of ligand analogs joined together covalently, normally to a hub nucleus. The hub nucleus is a polyfunctional material, normally polymeric, usually having a plurality of functional groups e.g. hydroxyl, amino, mercapto, ethylenic, etc. as sites for linking. The poly ligand analog well may be water soluble and will normally be at least about 30,000 molecular weight and may be 10 million or more molecular weight. Illustrative hub nuclei include polysaccharides, polypeptides (including proteins), nucleic acids, and the like.

Receptor—Any macromolecular organic compound or composition capable of recognizing a particular spatial and polar organization of a molecule e.g. epitopic or determinant site. The receptor will normally be at least as large as, usually much larger than, the specific organization to which the receptor binds, e.g. macromolecular. Illustrative receptors include naturally occurring receptors, antibodies, enzymes, Fab fragments, lectins, and the like. For any specific ligand, the receptor will be referred to as antiligand. The receptor-antiligand- and its reciprocal ligand form a specific binding pair.

Aggregate—A colloidal particle composed of a polymer of a member of the signal producing system, in which such member is incorporated independent of the occurrence of FBM-SBM binding and an enzyme is incorporated which is dependent upon such binding, resulting in a high multiple of the signal producing system member of the polymer to the enzyme.

Label—A compound which is either directly or indirectly involved with the production of a detectable signal and is bonded, either directly or indirectly, to ligand, ligand analog or receptor. In the subject invention, the labels will be components involved in the signal producing system, e.g. enzymes and reactants, and compounds employed in the linking system for forming the polymeric aggregation. The labels will therefore be distinguished between signal producing member labels and the linking labels.

Intermediate Substrate—The intermediate substrate is the product of one enzyme which acts as the substrate of the other enzyme.

Final Product—The product of the final reaction of the signal producing systems, which will be distinguishable from the substrate of the first enzyme, so that the formation of the Final Product will result in a change in a detectable signal in the assay. Usually, the Final Product will provide for a signal involving electromagnetic radiation, particularly involving ultraviolet or visible light, as a result of absorption or emission, as a result of fluorescence, chemiluminescence or phosphorescence.

Final Reactant—A compound capable of being polymerized and reacting with an enzyme product to result in a product which provides for a change in a detectable signal.

ASSAY

The subject assay is carried out at least in part in an aqueous zone at a moderate pH, generally close to optimum assay sensitivity. The aqueous assay zone in which the complexes are formed for the determination of analyte is prepared by employing an appropriate aqueous solution, normally buffered, the unknown sample which may have been subject to prior treatment, enzyme-SBM conjugate, the components of the linking system for the other enzyme and the remaining members necessary for the change in observable signal in the assay medium.

(Hereafter, when the two enzymes of the channeling system are referred to together, the two enzymes will be referred to as "enzyme+" and "enzyme*," so as to avoid any indication of which enzyme is the first enzyme in the series of enzyme reactions.)

For the most part, the analytes of interest will be polyepitopic. However, it is feasible to use the subject system for monoepitopic ligands, namely haptens. This can be achieved by preparing a poly(ligand analog), where the haptenic ligand and poly(ligand analog) will compete for available receptors, so that the degree of channeling which occurs will be dependent upon the amount of hapten present in the medium. Or, one could have a labeled hapten where the label provides for polyvalency.

In carrying out the assay an aqueous medium will normally be employed. Other polar solvents may also be employed, usually oxygenated organic solvents of from 1-6, more usually from 1-4 carbon atoms, including alcohols, ethers, amides and the like. Usually these cosolvents will be present in less than about 40 weight percent, more usually in less than about 20 weight percent. With polynucleotides, salts may be added, e.g. NaCl, generally at concentrations in the range of 0.1 to 1.5 M.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing proficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the assay and usually constant temperatures during the period of the assay. The temperatures for the determination will generally range from about 10°–60° C., more usually from about 15°–45° C.

The concentration of analyte which may be assayed will generally vary from about $10^{-4}$ to $10^{-15}$ M, more usually from about $10^{-6}$ to $10^{-14}$ M. Considerations as to whether the assay is qualitative, semi-quantitative or quantitative, the particular detection technique and the concentration of the analyte of interest will normally determine the concentration of other reagents.

While the concentrations of the various reagents will generally be determined by the concentration range of interest of the analyte, the final concentration of each of the reagents will normally be determined empirically to optimize the sensitivity of the assay over the range of interest. Based on binding sites of ligands and receptors, the ratio will usually not be greater than about $10^4$, usually not greater than about $10^2$. (A polynucleotide complementary sequence will be one binding site.) In referring to binding sites, this will usually, but not always, intend, where the ligand is polyepitopic, that one is concerned with all of the receptors which bind to a ligand. However, where there are two populations of receptors which do not compete for the same epitopic site, the ratios will be considered independently. The concentration of the members of the linking system will be varied widely, being determined empirically to provide for polymerization of the signal producing system member. Therefore, where the polymer is a copolymer, usually the ratio of comonomers will be relatively close to 1.

As indicated above, the concentration for each of the reagents will for the most part be determined empirically. The amount of each of the components involved in the signal change in the assay, namely substrates and cofactors for the enzymes, and Final Reactants, will be in sufficient amount so as not to be rate determining. Thus, the change in concentration of such components during the assay will not observably affect the rate of formation of Final Product.

The order of the addition of reagents may be varied, but will usually involve adding the enzyme-SBM conjugate and any other SBMs specific for the FBM analyte (or the complementary FBM to an SBM analyte), followed by the remaining members of the linking system and the components necessary for producing the Final Product. For receptor analyte the labeled ligand may be added initially to the sample followed by the addition of the remaining binding members, signal producing system members, and linking system members. On the other hand the sample and the enzyme$^+$-SBM conjugate can be incubated together in the assay medium before the addition of a non-enzymatic member of the linking system.

After sufficient time for aggregates to form, optionally a portion of the assay mixture may be transferred to a solid support, desirably a bibulous support or fibrous support. To the aggregates, either in solution or on a support, is added the developer, comprising the necessary reagents such as substrates and cofactors, to provide for a change in the observed signal.

In carrying out the assay, a sample containing the analyte will be obtained. The sample may be derived from a wide variety of sources and may be subject to prior treatment. Illustrative sources include physiological fluids, such as blood, serum, urine, lymph, spinal fluid, pus, mucous, etc. Other samples of cellular materials may be tissue cultures, lysates, DNA, RNA, membranes, etc. The sample need not be a physiological fluid or cellular but may be involved with monitoring contaminants in water, chemical processing, or the like. Depending upon the nature of the sample, as well as the nature of the analyte, the sample may be subjected to a wide variety of prior treatments which would be conventional as to the particular analyte.

Other than various conventional analytes in competitive protein binding assays or immunoassays, such as, lower molecular weight organic compounds e.g. drugs and synthetic chemicals, and macromolecules, such as polysaccharides, polypeptides and proteins, oligo- and polynucleotides may also serve as binding members. The polynucleotides may be derived from a wide variety of sources, including genomic, episomal, plasmid mitochondrial, synthetic, or the like. Where polynucleotides are involved, various prior treatments may be performed which involve cell lysis, gradient centrifugation, electrophoresis, etc.

For a listing of exemplary ligands, the description in U.S. Pat. No. 4,233,402, beginning at column 9, line 65, and ending at column 17, line 20, is incorporated herein by reference.

Similarly, the ligand analog is described in U.S. Pat. No. 4,233,402 beginning at column 17, line 21 and ending at column 18, line 12, which is incorporated herein by reference.

The reagents which are employed and can be provided in kits will comprise the enzyme$^+$-SBM conjugate, the linking system for linking the enzyme* of the enzyme pair to the polymeric aggregate or for lin king the Final Reactant, and the various components involved with the production of the detectable signal.

The first reagent to be discussed is the enzyme-SBM conjugate. The enzyme will usually be covalently bonded to the SBM. As already indicated the SBM will be a ligand, a receptor, usually a protein, e.g. antibody, or a polynucleotide, either polyribonucleotide or polydeoxyribonucleotide, being either the same or different sugar from the analyte. The polynucleotide SBM will have a sequence complementary to a sequence of the analyte and a linking chain, desirably an extended chain, covalently bonded to such sequence, which will allow for binding of enzymes to the SBM. The binding may be covalent between the enzyme and the SBM linking chain or non-covalent, for example, by employing antibody or one or a few sequences, complementary to a polynucleotide extended sequence covalently bonded to the enzyme or other receptors complementary to ligands bound to the extended chain.

In this way, one or a plurality of enzymes may be bound to the linking chain. Any complementary sequence will usually be at least about 6 bases, often being 10 bases or more. The extended sequence will be at least about 15 bases, usually 20 bases or more, and is conveniently a homopolymer, conveniently poly G or poly C.

Depending upon the nature of the SBM and the enzyme, there may be more than one enzyme per SBM, or more than one SBM per enzyme. Factors to be considered are the relative molecular weights, the nature of the enzyme, the effect of having a plurality of one or the other components on the functioning of either of the components, etc. Usually, the ratio of enzyme to SBM may vary from about 0.1–1000:1 or more. Various methods of linking are well known in the art. Any method may be employed which is satisfactory for providing the desired ratio and retaining the desired activity of the SBM and the enzyme.

In choosing an enzyme where two enzymes are employed, one must consider the fact that the enzyme must be a member of a pair, where the substrate of one enzyme is the product of the other enzyme and that the final result is to destroy or produce a product which allows for a differential signal in the assay medium. A number of enzyme systems are known which provide for this result and are described in U.S. Pat. No. 4,233,402.

The first type of enzymes to be considered is the oxidoreductases. These enzymes under the I.U.B. classification are Class 1. Of particular interest in this class are the groups of enzymes in 1.1.1 and 1.6, where nicotinamide adenine dinucleotide or its phosphate (NAD and NADP) are involved. These enzymes can be used to produce the reduced form of the coenzymes NADH and NADPH or vice versa. Specific enzymes include the dehydrogenases, such as alcohol dehydrogenase, glycerol dehydrogenase, lactate dehydrogenase, malate dehydrogenase, glucose-6-phosphate dehydrogenase, mannitol-1-phosphate dehydrogenase, glyceraldehyde-3-phosphate and isocitrate dehydrogenase.

Another group of enzymes in the oxidoreductase class are those that produce or destroy hydrogen peroxide. Among these enzymes are those of group 1.11.1, such as catalase and peroxidase, amino acid oxidase, glucose oxidase, galactose oxidase, uricase, polyphenol oxidase and ascorbate oxidase. Another oxidoreductase enzyme of interest is diaphorase.

Another group of enzymes of interest is the transferases, Class 2 of I.U.B. classification. particularly subclass 2.7, where phosphate is transferred to an alcohol, Class 2.7.1, e.g. hexokinase.

Another group of enzymes of interest is the hydrolases which are Class 3 in the I.U.B. classification. Of particular interest are the glycoside hydrolases (glycosidase), which are in Class 32.1 and phosphatases in Class 3.1.3. Of particular interest are α-amylase, cellulase, β-glucosidase, amyloglucosidase, β-galactosidase, amyloglucosidase, β-glucuronidase, acid phosphatase and alkaline. phosphatase.

Two additional groups of enzymes of interest are the lyases, in Class 4 and the isomerases in Class 5, particularly subclasses 5.3 and 5.4, which include enzymes such as phosphoglucose isomerase, triose phosphate isomerase and phosphoglucose mutase.

As illustrative of the manner of action of the various enzymes, the following examples are given. The first examples are concerned with the oxidoreductases, particularly those reducing NAD to NADH. These enzymes are for the most part dehydrogenases, where an hydroxylic group is taken to an oxo group. NADH then becomes an intermediate substrate which can be combined with a number of different enzymes to produce a product which may be detected. For example, the second enzyme can be diaphorase, which can react with a synthetic substrate, such as 2,6-dichlorophenolindophenol, methylene blue or potassium ferricyanide. The NADH can be employed with a flavoprotein, which includes such enzymes as glucose oxidase, amino acid oxidases and dihydroorotate dehydrogenase, where the product of the flavoprotein and NADH and oxygen, namely hydrogen peroxide, may then be detected.

Alternatively, one can use an oxidoreductase which produces hydrogen peroxide. Such enzymes include glucose oxidase, cytochrome reductase, uricase, and the like. These enzymes can be coupled with an enzyme which reacts with hydrogen peroxide, such as peroxidase, with the hydrogen peroxide reacting as the intermediate substrate. The hydrogen peroxide, plus the peroxidase, plus a luminescent material e.g. luminol, can be employed for producing a chemiluminescent reaction.

Hydrolases can be effectively used employing compounds, which require the hydrolytic removal of two substituents in two separate steps.

For example, 1-umbelliferyl-β-galactoside-6-phosphate must be converted to umbelliferone in order to obtain a fluorescent signal. By employing alkaline phosphatase as the first enzyme, 1-umbelliferyl-β-galactoside as the intermediate substrate, and β-galactosidase as the second enzyme, one can obtain a detectable signal-fluorescence-which will be dependent upon the proximity of the two labels in a complex. Both enzymes are essential to the formation of umbelliferone which provides the detectable signal.

Alternatively, the hydrolase may produce a product which may then be used in a subsequent enzymatic reaction. For example, a coenzyme may be functionalized so as to inhibit its activity and the functionality be removable by a hydrolase enzyme and the free coenzyme then able to interact with the second enzyme to produce a detectable signal.

In addition, isomerases can be used to produce a substrate for a subsequent enzymatic reaction, particularly with saccharides, isomerizing aldoses and ketoses by transferring a phosphate from one position to another.

While the enzyme channeling system is by far preferred, it is feasible to have a reactant which can react with the product of the first enzyme to provide for a change in a detectable signal. For example, one could employ derivatives of Ellman's reagent, where the disulfide is linked to a compound which allows for polymerization, e.g. biotin, which can be polymerized with avidin by employing an enzyme such as cholinesterase, one could release thioacetic acid, which would react with Ellman's reagent to produce carboxynitrophenyl-thiophenoxide, which would provide an observable signal. Alternatively, one could employ an enzyme which produces hydrogen peroxide and employ as the Final Reactant, a chelated metal catalyst which destroys the hydrogen peroxide. One can then measure the hydrogen peroxide which is present in the assay medium. Other combinations could include employing NAD and a dehydrogenase, where the resulting NADH would react with a compound to form or destroy a color, e.g. Meldola blue. Other combinations are also available.

The next group of reagents are the linking system. The linking system involves combinations of covalent or non-covalent linking members having specificity for each other, that is, having specific reactivity or being homologous or cognate ligands and receptors. The linking system permits the binding of a large plurality of enzymes to the complex between the FBM and the enzyme-SBM conjugate by polymerizing the enzyme and associating the complex with the enzyme polymer. Various linking techniques can be employed, both covalent and non-covalent, preferably non-covalent.

The concept is to polymerize most of one of the enzymes into large aggregates and to associate the other enzyme with such aggregate through the complex of the FBM and the enzyme-SBM conjugate, particularly by binding to the FBM.

The members of the linking system are polyvalent, being at least divalent. The polyvalency may be as a result of a plurality of reactive functionalities, which under the conditions of the assay will form bonds which substantially preclude the binding of the enzyme-SBM conjugate to the polymeric enzyme aggregate through other than the binding to the FBM.

Alternatively, non-covalent binding can be employed, where homologous ligands and receptors form copolymers by having a plurality of epitopic or determinant sites on the enzyme, either naturally present or synthetically introduced, and a polyvalent receptor having a plurality of binding sites specific for the sites present on the enzyme.

In the course of the polymerization rapid diffusion of the enzymes to the growing polymer results to produce large aggregations of the enzyme, while substantially depleting the bulk solution of the enzyme. In addition, as the aggregation of the enzyme is formed, enzyme-SBM bound to FBM is bound to the aggregation so as to bring the two enzymes involved in the channeling in close proximity to each other, with one of the enzymes preferably in substantial mole excess to the enzyme of the enzyme-SBM conjugate.

Among non-covalent techniques for linking, various receptors may be employed. One system can involve common determinant sites of a label on a receptor for the ligand ("antiligand") and a multivalent receptor which recognizes these common determinant sites. The common determinant sites may be the determinant sites of an enzyme label, where the enzyme is bound to receptor and optionally additional enzyme is added which is not covalently bonded to receptor. Or determinant sites may be introduced by covalently bonding various compounds, particularly low molecular weight organic compounds, to the antiligand and to the enzyme. Illustrative of such compounds are biotin, which may be used with its naturally occurring receptor, avidin; thyroxine, which may be used with thyroxine binding globulin; methotrexate, which may find use with dihydrofolate reductase, etc.

Alternatively, one could use antibodies from various host sources, e.g. rabbit, sheep, or the like, and then use antibodies against such host immunoglobulin to act as the polymerizing system. For example, one could have an enzyme-sheep anti-ligand conjugate to which is added rabbit anti-(sheep immunoglobulin), wherein the enzyme-SBM conjugate incorporates a receptor other than sheep immunoglobulin for the SBM.

Where polynucleotides are involved, an enzyme-antibody conjugate can be employed, where the antibody is directed to an epitope of the analyte that is absent in the SBM, for example an antibody directed to single stranded polynucleotide having the sugar of the analyte i.e. DNA or RNA. In this way the sequences other than the sequence of interest, in conjuction with the sequence of interest, will form large three dimensional aggregates of one of the enzymes about the complex between the analyte nucleotide sequence and the enzyme-SBM conjugate. For example, with a DNA sequence of interest, the SBM will be RNA complementary to the DNA analyte and will be linked to an extended polyribonucleotide to which one or more of the same enzyme is bound, either covalently or through RNA-RNA coupling or through anti-RNA-binding to RNA. By adding enzyme*-antiDNA conjugate, the DNA present in the assay medium can copolymerize with the enzyme*—antiDNA to form a large aggregate which will include the DNA analyte—(RNA-enzyme+) hydridization product, so as to have a large amount of enzyme* in close proximity to enzyme+.

For covalent bonding, various reactive combinations can be employed, which while individually stable in the assay medium will specifically and preferentially form covalent bonds under predetermined conditions. One reactant will be on one member and the other reactant on the other member. Illustrative combinations include active halogen e.g. bromoacetyl, and thiol groups, activated ethylenes, e.g. maleimidyl and thiol groups, thiols and Ellman's reagent derivatives, thiols and bis-arylmercury halides etc. One or a plurality of the groups may be covalently bonded to a reciprocal binding member for the FBM. For example, the enzymes may be functionalized with maleimide groups and antibodies functionalized with mercaptans. Where the enzyme-SBM conjugate has groups which may interact e.g. thiol groups, these may be capped so as to prevent any reaction during the assay. For forming disulfides mercaptans may be used and a mild oxidant, e.g. hydrogen peroxide, added or may be present as a product of an enzyme reaction.

By employing the linking system, one can sweep large amounts of enzyme or Final Reactant from the assay medium and bring these signal producing system members into proximity to the enzyme-SBM conjugate and ligand complex. Thus, one can obtain high amplification of signal, while enjoying the benefits of rates of diffusion in an aqueous medium. In this manner, one achieves a uniformly dispersed aggregate while maintaining a stable dispersion, which allows for signal determination in an aqueous medium without separation of enzyme-SBM conjugate bound to FBM and unbound enzyme-SBM conjugate. Alternatively, one can separate the aggregates on a porous pad or filter before adding the reagents necessary for signal production.

The remaining third group of substances employed in the assay are the members of the signal producing system, namely the substrates and cofactors which provide for the change in signal in the assay medium. The change in signal may be as a result of a change in light absorption, a change in fluorescence, chemiluminescence, or other change in the effect of the system on electromagnetic radiation or changes in other properties such as electro-chemical. For the most part, the detectable signal will be a light signal, either ultraviolet or visible light. Because the substrates will vary with the particular enzymes employed, and for most, if not all, commercially available enzymes, substrates have been described or are generally available which provide for the production of product which can be detected spectrophotometrically or fluorometrically, many of these substances or derivatives thereof may be used by providing for an appropriate combination of enzymes.

In some situations, it will be desirable to provide for a scavenger of the product of the first enzyme. For example, where hydrogen peroxide is the product, catalase may be introduced into the medium, so as to ensure a very low or insignificant concentration of hydrogen peroxide in the bulk medium.

Various ancillary materials will be employed, particularly buffers, stabilizers, proteins, surfactants, more particularly non-ionic surfactants, or the like. These may function in providing specific properties to the assay medium, such as maintaining a desired pH, inhibiting non-specific binding, imparting stability to the reagents during storage either as a lyophilized product or in an aqueous medium, or the like.

Desirably, the reagents can be provided as kits so that the specific ratios are optimized to provide for optimum sensitivity over the concentration range of interest of the analyte. The kits will include either in combination in the same container or separately, in different containers, the enzyme-SBM conjugate, the members of the linking system, the enzyme substrates and cofactors, the Final Reactant, as appropriate, the ancillary members described above, bulking factors, etc.

The following examples are offered by way of illustration and not by way of limitation.

EXPERIMENTAL EXAMPLE 1

Coupling of horseradish peroxidase (HRP) to Antibody

To 150 mg HRP (Sigma Lot 31F9605) in 20 ml distilled water, pH 5.3, was added 4 ml of 0.1 M sodium periodate in distilled water and the mixture stirred for 20 min. at room temperature. After adding 2.4 ml 1 M glycerol, the solution was stirred for 30 min. at room temperature and then dialyzed against 2 mM sodium acetate, pH 4.5, 3×500 ml, 2 hr., overnight, 2 hr.

A sample of antibody to polyribosephosphate (3 ml, Sample N-2, Lot 28A) was diluted to 9 ml and dialyzed against 3×10 mM sodium carbonate, pH 9.5, 2 hr., overnight, 2 hr.

The oxidized HRP sample was diluted 1:20 in 0.1 M sodium phosphate, pH 6.0 (HRP—$1.072 \times 10^{-4}$ M=4.3 mg/ml, based on absorption at 403 nm) to provide a final solution at a concentration of 3.13 mg/ml. A reaction mixture was prepared of 21.64 ml oxidized HRP and 4.67 ml of the above antibody, the solution diluted to 29.7 ml with 10 mM sodium carbonate, and the pH then adjusted to 9.6 with 0.1 N sodium hydroxide. The reaction mixture was then stirred for 2 hrs. at room temperature, followed by cooling to 0° C. on ice and then 1.5 ml (4 mg/ml) sodium borohydride added. The reaction was protected from light by aluminum foil. After stirring for 2 hrs. at 0° C. the reaction mixture was dialyzed overnight against 1 L PBS (10 mM sodium phosphate, pH 7.2, 0.15 M NaCl).

The conjugate was concentrated to 3.5–4.5 ml using a collodion apparatus. The concentrate was then chromatographed on a Biogel A5M column, 2.5×90 cm and 5 ml fractions collected. The effluent was monitored for transmission at 280 nm and the protein eluted with PBS containing 0.01% sodium azide. The column was run at 20 ml/hr. pooling fractions 39–48, 49–57, 58–61 and 62–66 to provide pools 1–4 respectively.

EXAMPLE 2

Conjugation of glucose oxidase to antipolyribose phosphate (antiPRP)

Glucose oxidase (40 ml Lot. 61F 9007) was dialyzed against 1 L each 3×0.3 M sodium bicarbonate (3 hr., overnight, 3 hr.). (Initial concentration of the glucose oxidase was 5.3 mg/ml.) After completion of the dialysis, a 0.2 ml aliquot was removed and the remainder treated with 1-fluoro-2,4-dinitrobenzene. The remaining volume, 35 ml, pH 8.23, was combined with 3.5 ml 1% (w/v) of 1-fluoro-2,4-dinitrobenzene in abs. ethanol. After stirring for 1 hr. at room temperature, the reaction mixture was dialyzed overnight against 1 L 0.3 M sodium bicarbonate and the next day the dialysis repeated with 1 L of fresh bicarbonate for 3 hrs. The sample was then concentrated to about 20 ml using a collodion apparatus.

To the concentrated capped glucose oxidase was added 0.4 M sodium periodate in distilled water and the solution stirred for 20 min. at room temperature. To the reaction mixture was then added 1.1 ml of 1 M glycerol in water and the solution was stirred for an additional hour at room temperature. The solution was then dialyzed 3×10 mM sodium carbonate, pH 9.6 (3 hr., overnight, 3 hr., 600 ml each change), the residue having a volume of 27.5 ml.

AntiPRP (1.2 ml New York State Department of Health Lot 28A) was diluted to 3.6 ml with 10 mM sodium carbonate, pH 9.6, and the diluted sample dialyzed against 3×10 mM sodium carbonate, pH 9.6, 3 hr., overnight, 3 hr., 300 ml each change), leaving a final volume of 3.2 ml. The concentration determined by ultraviolet absorption at 280 nm was 28.7 mg/ml.

To 27.5 ml of the capped glucose oxidase was added the antibody sample prepared above and the solution stirred for 14 hr., at room temperature, followed by cooling to 0° C. on ice. To the reaction mixture was then added 1.55 ml of 4 mg/ml sodium borohydride in distilled water, while the solution was protected from light and stirred for 2 hr. at room temperature. At the end of this time, the reaction mixture was dialyzed against 1 L PBS for 3 hrs. at room temperature.

The PBS solution was concentrated to 5 ml using a collodion apparatus and then loaded onto a 2.5×90 cm Biogel A5M column chromatographing as described previously and collecting fractions which were pooled as follows 40–45; 46–50; 51–56; 57–60; and 61–63, monitoring the fractions at 280 nm and 450 nm, to provide pools 1–5 respectively.

To demonstrate the sensitivity and effectiveness of the subject technique, the following study was carried out. The enzyme reagents were prepared by diluting 1:40 pool 2 of the glucose oxidase conjugate (Example 2) and 1:32 of pool 1 of the HRP conjugate (Example 1). The buffer employed was PBS-Tween (10 mM sodium phosphate, pH 7.2, 150 mM NaCl, 0.05% w/v Tween 20). To 10 microtiter wells was added 10 μl each of each of the enzyme conjugates and 10 μl of serially diluted PRP, using two-fold dilutions and ranging from 500 ng/ml to 0.5 ng/ml was added to nine of the wells plus a blank for the 10th well. The plate was then covered and incubated for 10 mins. at 37° C. To the mixture was then added 10 μl of 1:50 diluted sheep antibody to amino modified glucose oxidase in PBS-Tween buffer.

The mixture was then incubated for 60 mins. at 37° C. with shaking, followed by the addition of 220 µl of a developer solution (250 mM glucose, 10 mM ABTS (2,2'-azino-di-3-ethylbenzthiazoline sulfonic acid), 0.8 mg/ml ovalbumin and 185 µg/ml catalase). The mixture was shaken at 37° C. for 11 mins. and read in the Artek vertical beam microtiter plate reader at 415 nm. The results of the readings are set forth in the following table.

TABLE 1

| PRP conc. ng/ml | Mean Artek reading ± SD (avg. of 6) | Artek reading corrected for blank |
|---|---|---|
| 500 | 1.4285 ± 0.0818 | 0.7053 |
| 250 | 1.2893 ± 0.0366 | 0.5661 |
| 100 | 1.1243 ± 0.0499 | 0.4011 |
| 50 | 0.9680 ± 0.0358 | 0.2448 |
| 25 | 0.8772 ± 0.0246 | 0.1540 |
| 10 | 0.8013 ± 0.0160 | 0.0780 |
| 5 | 0.7610 ± 0.0156 | 0.0378 |
| 1 | 0.7600 ± 0.009 | 0.0368 |
| 0.5 | 0.7113 ± 0.0132 | — |
| Blank | 0.7232 ± 0.0175 | 0 |

The above procedure was modified in a second assay. Using the same reagents and materials as described previously, the assay mixture of the two conjugates and PRP were placed in 10×75 mm glass tubes, the mixture incubated at 37° for 10 min. with shaking, followed by the addition of the sheep anti(amine modified glucose oxidase) and the tubes incubated for an additional 30 min. at 37° with shaking.

At the end of this time, 270 µl of PBS-Tween buffer was added to each tube, the tube vortexed and 100 µl of the tube contents was then spotted out on an 8×8 mm pad of glass fiber paper placed on a second larger glass fiber pad. Onto the spot was then added 3 ml of the developer solution described previously to wash away unbound conjugates and to initiate development of the colored product. Each pad was developed for 2.5 min. and then washed with 270 µl PBS-Tween buffer . and pressed dry. A concentration of 0.5 ng/ml, the lowest concentration employed, was detectable. However, development continued for some time after washing and pressing dry of the pad, so that eventually color appeared on the blank. Even after standing for an extended period, one could readily distinguish 25 ng/ml PRP from no PRP.

The above described experiment was repeated except that incubation with anti(amino modified glucose oxidase) was for 60 min. and development was for 440 sec. Similar results were obtained.

It is evident from the above results, that the subject method provides for a rapid, sensitive assay which can be carried out in a variety of ways. By fairly simple manipulations, extremely low concentrations of analytes may be obtained. By employing a linking means which provides for high localized concentration of one enzyme as compared to another enzyme, particularly where the highly concentrated enzyme provides the substrate for the second enzyme, the rate of production of a product which can be detected can be greatly enhanced. Thus, extremely low concentrations of analyte can be detected by virtue of producing a strong signal in relation to a background signal. Quantitative results can be obtained by using instruments such as a spectrophometer or reflectometer, while semi-quantitative or qualitative results can be obtained visibly, particularly where control is employed so as to provide a comparison.

Although the foregoing invention has been described in some detail by way of illustration and example for purposes of clarity of understanding, it will be obvious that certain changes and modifications may be practiced within the scope of the appended claims.

What is claimed is:

1. A method for detecting the presence of an analyte in a sample suspected of containing said analyte, when said analyte is a member of a specific binding pair consisting of first and second binding members ("FBM" and "SBM", respectively), said method employing a channeling signal producing system comprising an enzyme, designated as enzyme+, conjugated to an SBM to provide enzyme+-SBM conjugate, an enzyme substrate and a Final Reactant, wherein said Final Reactant is (1) another enzyme, designated as enzyme*, where the two enzymes are related by the substrate of one enzyme being the product of the other enzyme, or (2) a compound which reacts with the product of enzyme+, wherein the reactions of said enzyme+ in conjunction with enzyme* or said compound results in a change in an observable signal in relation to the amount of analyte in said sample; and linking system providing for the polymerization of said Final Reactant and the incorporation of enzyme+ within the polymer as a function of the binding of enzyme+-SBM conjugate to FBM so as to form a polymeric channeling aggregate;

said method comprising:

combining in an aqueous assay medium;

(a) said sample;

(b) said enzyme+-SBM conjugate, and FBM when said analyte is a SBM, so as to form a complex between said FBM and said enzyme+-SBM conjugate in relation to the amount of analyte present;

(c) any members of said linking system, whereby there is formed a polymeric channeling aggregate of said Final Reactant and a complex of enzyme+-SBM conjugate with FBM; and (d) remaining members of a signal producing system, whereby a Final Product is produced as a result of channeling of said members of said signal producing system in said polymeric channeling aggregate, which results in a change in a detectable signal; and comparing said detectable signal to the detectable signal observed in an assay medium having a known amount of analyte.

2. A method according to claim 1, wherein said linking system comprises enzyme*-SBM conjugate and anti-enzyme*.

3. A method for detecting the presence of an analyte in a sample suspected of containing said analyte, wherein said analyte is a member of a specific binding pair consisting of first and second binding members ("FBM" and "SBM" respectively), said method employing (1) enzyme channeling where two enzymes, enzyme+ and enzyme*, which are members of a signal producing system are employed, where the product of one enzyme is the substrate of the other enzyme, and enzyme+ is conjugated to a SBM to provide enzyme+-SBM conjugate; (2) a linking system providing for the polymerization of enzyme* and the incorporation of enzyme+ through the binding of a complex of enzyme+-SBM conjugate to FBM to form a polymeric channeling aggregate; and (3) the remaining members of the signal producing system comprising substrates, including cofactors, of said enzymes, which results in a change in a detectable signal as a result of the formation of said polymeric channeling aggregate in relation to the amount of analyte present;

said method comprising:

combining in an aqueous assay medium;
(a) said sample;
(b) said enzyme+-SBM conjugate, and FBM wherein said analyte is a SBM, so as to form a complex between said FBM and said enzyme+-SBM conjugate in relation to the amount of analyte present;
(c) members of said linking system, whereby is formed a polymeric channeling aggregate of enzyme* and the complex of enzyme+-SBM conjugate with FBM; and
(d) members of the signal producing system, whereby a Final Product is produced as a result of enzyme channeling of said members of said signal producing system in said polymeric channeling aggregate, which results in a change in a detectable signal; and comparing said detectable signal to the detectable signal observed in an assay medium having a known amount of analyte.

4. A method according to claim 3, wherein said FBM is a ligand and said SBM is a receptor.

5. A method according to claim 4, wherein said SBM is an antibody.

6. A method according to any of claims 3, 4 or 5, wherein said linking system comprises enzyme*-SBM conjugate and anti-enzyme*.

7. A method according to any of claims 3, 4, or 5, wherein said linking system comprises modified enzyme*-SBM conjugate, where said modification is the bonding of ligands to said conjugate, and polyvalent receptor for said ligand.

8. A method according to claim 3, wherein said enzymes are oxidoreductases.

9. A method according to claim 3, wherein said assay medium is transferred to a porous support prior to the addition of said signal producing system to said polymeric channeling aggregates.

10. A method according to claim 3, wherein said sample and said enzyme+-SBM conjugate are incubated together in said assay medium before the addition of a non-enzymatic member of said linking system.

11. A method for detecting the presence of an analyte in a sample suspected of containing said analyte, wherein said analyte is a member of a specific binding pair consisting of ligand and receptor;

said method employing (1) enzyme channeling where two oxidoreductase enzymes, enzyme+ and enzyme*, are employed, which are members of a signal producing system; where the product of one enzyme is the substrate of the other enzyme; and where enzyme+ is present conjugated to a first receptor, enzyme+-first receptor conjugate wherein first receptors bind to ligand; (2) a linking system providing for the polymerization of enzyme*, comprising enzyme* conjugated to first receptor, enzyme*-first receptor conjugate, wherein said enzyme*-first receptor conjugate has naturally occurring determinant sites or such sites are synthetically introduced, and a polyvalent second receptor for said determinant sites, whereby polymerization of enzyme* and the incorporation of enzyme+ through the binding of a complex of enzyme+-first receptor conjugate to ligand occurs to form a polymeric channeling aggregate; and (3) a signal producing system comprising substrates, including cofactors, of said enzymes, which results in the production of a final product which provides a change in a detectable signal as a result of the formation of said polymeric channeling aggregate in relation to the amount of analyte present;

said method comprising:

combining in an aqueous medium;
(a) said sample;
(b) said enzyme+-first receptor conjugate, and ligand when said analyte is a receptor, to form an enzyme+-first receptor and ligand complex;
(c) enzyme*-first receptor and second receptor for polymerizing enzyme*, whereby enzyme* is polymerized and incorporates enzyme+ as part of said complex;
(d) members of the signal producing system, whereby said members in conjunction with the channeling of said enzymes produce a Final Product providing a detectable signal in an amount related to the amount of analyte present; and comparing said detectable signal to the detectable signal observed in an assay medium having a known amount of analyte.

12. A method according to claim 11, wherein additional enzyme* is added as a member of said linking system.

13. A method according to any of claims 11 or 12, wherein one of said enzymes is glucose oxidase and the other of said enzymes is horseradish peroxidase.

14. A kit useful in a method according to any of claims 3, comprising enzyme+-SBM conjugate and a linking system including as one component, enzyme*, where enzyme+ and enzyme* are related by the substrate of one being the product of the other, and means for polymerizing enzyme*.

15. A kit according to claim 14, wherein said linking system comprises enzyme*-receptor conjugate and receptor for enzyme* or a ligand bound to enzyme*.

16. A kit useful in a method according to claim 11, comprising enzyme+-first receptor conjugate and a linking system including as one component, enzyme*, where enzyme+ and enzyme* are related by the substrate of one being the product of the other, and means for polymerizing enzyme*.

17. A kit according to claim 16, wherein said linking system comprises enzyme*-receptor conjugate and receptor for enzyme* or a ligand bound to enzyme*.

* * * * *